United States Patent
Menne et al.

(10) Patent No.: US 9,439,430 B2
(45) Date of Patent: Sep. 13, 2016

(54) METHOD OF CONTROLLING RESISTANT HARMFUL PLANTS

(71) Applicant: BAYER CROPSCIENCE AG, Monheim (DE)

(72) Inventors: Hubert Menne, Mainz-Kastel (DE); Werner Schlesinger, Floersheim (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 14/647,848

(22) PCT Filed: Dec. 3, 2013

(86) PCT No.: PCT/EP2013/075301
§ 371 (c)(1),
(2) Date: May 28, 2015

(87) PCT Pub. No.: WO2014/086736
PCT Pub. Date: Jun. 12, 2014

(65) Prior Publication Data
US 2015/0373977 A1 Dec. 31, 2015

(30) Foreign Application Priority Data

Dec. 6, 2012 (EP) ..................................... 12195951

(51) Int. Cl.
| | | |
|---|---|---|
| *A01N 43/66* | (2006.01) | |
| *A01N 43/68* | (2006.01) | |
| *A01N 43/54* | (2006.01) | |
| *A01N 43/653* | (2006.01) | |

(52) U.S. Cl.
CPC .............. *A01N 43/68* (2013.01); *A01N 43/54* (2013.01); *A01N 43/653* (2013.01); *A01N 43/66* (2013.01)

(58) Field of Classification Search
None
See application file for complete search history.

(56) References Cited

U.S. PATENT DOCUMENTS

| | | |
|---|---|---|
| 5,476,936 A | 12/1995 | Philipp et al. |
| 5,580,842 A | 12/1996 | Philipp et al. |
| 5,696,257 A | 12/1997 | Philipp et al. |
| 5,847,126 A | 12/1998 | Philipp et al. |
| 8,236,729 B2 | 8/2012 | Hacker et al. |
| 8,426,342 B2 | 4/2013 | Kilian et al. |
| 2006/0014642 A1 | 1/2006 | Hacker et al. |
| 2010/0016158 A1 | 1/2010 | Kilian et al. |
| 2010/0048400 A1 | 2/2010 | Kraehmer et al. |
| 2013/0005568 A1* | 1/2013 | Strachan ............... A01N 37/46 504/100 |

FOREIGN PATENT DOCUMENTS

| | | |
|---|---|---|
| DE | 4336875 A1 | 3/1995 |
| EP | 02147600 A1 | 1/2010 |
| WO | 2006007947 A1 | 1/2006 |
| WO | 2008101588 A2 | 8/2008 |

OTHER PUBLICATIONS

International Search Report from corresponding PCT/EP2013/075301, mailed Mar. 20, 2014.
"The Pesticide Manual", Aug. 15, 2009, British Crop Protection Council, http://www.alanwood.net/pesticides/index_cn_frame.html.
http://www.alanwood.net/pesticides/flazasulfuron.html, May 26, 2015. (6 pages).

* cited by examiner

*Primary Examiner* — Alton Pryor
(74) *Attorney, Agent, or Firm* — McBee Moore Woodward Vanik IP, LLC

(57) ABSTRACT

A method for controlling harmful plants resistant to active compounds from the group of the inhibitors of acetolactate synthase, acetyl coenzyme A carboxylase, photosynthesis at photosystem II, microtubuli arrangement, cell division or 5-enolpyrovylshikimate-3-phosphate synthase, in particular acetolactate synthase, is described.

15 Claims, No Drawings

METHOD OF CONTROLLING RESISTANT HARMFUL PLANTS

CROSS REFERENCE TO RELATED APPLICATIONS

This application is a §371 National Stage Application of PCT/EP2013/075301, filed 3 Dec. 2013, which claims priority to EP 12195951.4, filed 6 Dec. 2012.

BACKGROUND

1. Field of the Invention

The invention is in the field of crop protection compositions employed against resistant harmful plants.

2. Description of Related Art

In recent years, on agriculturally utilizable areas, there have increasingly been harmful plants resistant to numerous active compounds from the group of the inhibitors of acetolactate synthase, acetyl coenzyme A carboxylase, photosynthesis at photosystems I+II, auxins, protoporphyrinogen oxidase or 5-enolpyrovylshikimate-3-phosphate synthase and others. In agricultural practice, the control of these harmful plants is found to be increasingly problematic.

WO 2006/007947 A1 discloses, inter alia, herbicidal compositions comprising indaziflam and flazasulfuron, rimsulfuron, foramsulfuron. A particular suitability of these herbicidal compositions for controlling resistant harmful plants is not disclosed in this publication.

SUMMARY

It is an object of the present invention to provide herbicidal compositions for controlling such resistant harmful plants. It has now been found that herbicidal compositions comprising indaziflam and a further herbicidally active compound are particularly suitable for this purpose. The present invention provides a method for controlling harmful plants resistant to active compounds from the group of the inhibitors of acetolactate synthase, acetyl coenzyme A carboxylase, photosynthesis at photosystem II, microtubuli arrangement, cell division or 5-enolpyrovylshikimate-3-phosphate synthase, in particular acetolactate synthase, characterized in that a herbicidal composition comprising A) indaziflam (A) and
B) a herbicidally active compound from the group consisting of flazasulfuron (B1), foramsulfuron (B2), rimsulfuron (B3), chlorimuron-ethyl (B4) and thiencarbazone-methyl (B5) is employed.

Herbicidal compositions comprising indaziflam and chlorimuron-ethyl are novel and also form part of the subject matter of the present invention.

The active compounds indaziflam, flazasulfuron, foramsulfuron, rimsulfuron, chlorimuron-ethyl and thiencarbazone-methyl are known, for example, from "The Pesticide Manual" 15th edition, 2009, British Crop Protection Council, and from the website "http://www.alanwood.net/pesticides/index_cn_frame.html".

DETAILED DESCRIPTION OF A PREFERRED EMBODIMENT

The active compounds of the herbicidal compositions to be used in accordance with the invention are usually employed in the following dosages.

Indaziflam: 10 to 200, preferably 10 to 150, with preference 10 to 100 g/ha.

Flazasulfuron, foramsulfuron, rimsulfuron, chlorimuron-ethyl and thiencarbazone-methyl: in each case 2.5 to 100, preferably 2.5 to 75, with preference 2.5 to 40 g/ha.

The ratios of the active compounds (A) and (B) can be found by looking at the application rates mentioned for the individual compounds. For example, the ratios (A):(B) in the range from 10:1 to 1:10, with preference from 5:1 to 1:5, are of particular interest.

Surprisingly, the herbicidal compositions to be used in accordance with the invention have high synergistic activity against resistant harmful plants. Here, it is particularly surprising that the herbicidally active compounds of group (B), which are known as inhibitors of acetolactate synthase, have, in combination with the herbicidally active compound (A), high synergistic activity against harmful plants resistant to inhibitors of acetolactate synthase. Therefore, these herbicidal compositions are highly suitable for use for controlling resistant harmful plants. Thus, the present invention furthermore provides the use of these herbicidal compositions for controlling resistant harmful plants.

Furthermore, the combinations according to the invention can be employed together with other active compounds, for example from the group of the safeners, fungicides, insecticides and plant growth regulators, or from the group of additives and formulation aids customary in crop protection. Additives are, for example, fertilizers and colorants.

The herbicidal compositions to be used in accordance with the invention have excellent herbicidal activity against a broad spectrum of economically important monocotyledonous and dicotyledonous harmful plants which have become resistant, in particular, to inhibitors of acetolactate synthase. These include, for example, *Alopecurus* spp., *Amaranthus* spp., *Apera* spp., *Bidens* spp., *Bromus* spp., *Erigeron* spp., *Euphorbia* spp., *Chenopodium* spp., *Kochia* spp. and *Lolium* spp.

When herbicidally active compounds of groups (A) and (B) are applied jointly, superadditive (=synergistic) effects occur. Here, the activity in the combinations is higher than the expected sum of the activities of the individual herbicides employed. The synergistic effects allow the application rate to be reduced, a broader spectrum of harmful plants to be controlled, a more rapid onset of the herbicidal action, a longer persistency, a better control of the harmful plants with only one or a few applications and a widening of the application period possible. In some cases, employing the compositions also reduces the amount of harmful ingredients such as nitrogen or oleic acid in the crop plant. The abovementioned properties and advantages are required in the practical control of harmful plants to keep agricultural crops free of unwanted competing plants, and thus to ensure and/or increase yield levels from the qualitative and quantitative angles.

The herbicidal compositions to be used in accordance with the invention can be present both as mixed formulations of the two active compounds (A) and (B), if appropriate with further active compounds, additives and/or customary formulation aids which are then applied in a customary manner diluted with water, or can be prepared as so-called tank mixes by joint dilution of the separately formulated or partially separately formulated components with water.

The active compounds (A) and (B) or their combinations can be formulated in various ways according to which biological and/or physicochemical parameters are required. Examples of general formulation options are: wettable powders (WP), emulsifiable concentrates (EC), aqueous solutions (SL), emulsions (EW) such as oil-in-water and waterin-oil emulsions, sprayable solutions or emulsions, oil- or water-based dispersions, suspoemulsions, dusts (DP), seed-dressing products, granules for soil application or application by broadcasting or water-dispersible granules (WG), ULV formulations, microcapsules or waxes.

The individual types of formulation are known in principle and are described, for example, in: Winnacker-Kuchler, "Chemische Technologie" [Chemical Technology], Volume 7, C. Hanser Verlag Munich, 4th ed. 1986; van Valkenburg, "Pesticide Formulations", Marcel Dekker, N.Y., 1973; K. Martens, "Spray Drying Handbook", 3rd ed. 1979, G. Goodwin Ltd. London.

The necessary formulation aids, such as inert materials, surfactants, solvents and further additives are likewise known and are described, for example, in: Watkins, "Handbook of Insecticide Dust Diluents and Carriers", 2nd Ed., Darland Books, Caldwell N.J.; H.v. Olphen, "Introduction to Clay Colloid Chemistry"; 2nd ed., J. Wiley & Sons, N.Y. Marsden, "Solvents Guide", 2nd ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976, Winnacker-Küchler, "Chemische Technologie", volume 7, C. Hanser Verlag Munich, 4th ed. 1986. Based on these formulations, it is also possible to produce combinations with other pesticidally active substances such as other herbicides, fungicides or insecticides, and also with safeners, fertilizers and/or growth regulators, for example in the form of a finished formulation or as a tank mix.

Wettable powders are preparations which can be dispersed uniformly in water and, as well as the active compound, apart from a diluent or inert substance, also comprise surfactants of the ionic or nonionic type (wetting agents, dispersants), for example polyoxyethylated alkylphenols, polyethoxylated fatty alcohols or polyethoxylated fatty amines, alkanesulphonates or alkylbenzenesulphonates, sodium lignosulphonate, sodium 2,2'-dinaphthylmethane-6, 6'-disulphonate, sodium dibutylnaphthalenesulphonate or else sodium oleoylmethyltaurinate.

Emulsifiable concentrates are prepared by dissolving the active compound in an organic solvent, for example butanol, cyclohexanone, dimethylformamide, xylene or else relatively high-boiling aromatics or hydrocarbons with addition of one or more ionic or nonionic surfactants (emulsifiers). The emulsifiers used may, for example, be: calcium alkylarylsulphonates such as calcium dodecylbenzenesulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan fatty acid esters, polyoxyethylene sorbitan fatty acid esters or polyoxyethylene sorbitol esters.

Dusts are obtained by grinding the active compound with finely distributed solid substances, for example talc, natural clays, such as kaolin, bentonite and pyrophyllite, or diatomaceous earth.

Granules can be produced either by spraying the active compound onto adsorptive granulated inert material or by applying active compound concentrates by means of adhesives, for example polyvinyl alcohol, sodium polyacrylate or mineral oils, to the surface of carrier substances, such as sand, kaolinites or of granulated inert material. Suitable active compounds can also be granulated in the manner customary for the production of fertilizer granules—if desired as a mixture with fertilizers. Water-dispersible granules are produced generally by processes such as spray-drying, fluidized bed granulation, pan granulation, mixing with high-speed mixers and extrusion without solid inert material.

The agrochemical preparations generally comprise from 0.1 to 99% by weight, in particular from 2 to 95% by weight, of active compounds (A) and/or (B), the following concentrations being customary, depending on the type of formulation:

In wettable powders, the active compound concentration is, for example, from about 10 to 95% by weight, the remainder to 100% by weight consisting of customary formulation components. In the case of emulsifiable concentrates, the active compound concentration can be, for example, from 5 to 80% by weight.

In most cases, formulations in the form of dusts comprise from 5 to 20% by weight of active compound, sprayable solutions comprise about 0.2 to 25% by weight of active compound.

In the case of granules such as dispersible granules, the active compound content depends partially on whether the active compound is present in liquid or solid form and on which granulation auxiliaries and fillers are used. In water-dispersible granules the content is generally between 10 and 90% by weight.

In addition, the active compound formulations mentioned optionally comprise the respective customary adhesives, wetting agents, dispersants, emulsifiers, preservatives, antifreeze agents and solvents, fillers, colorants and carriers, antifoams, evaporation inhibitors and pH- or viscosity-modifying agents.

For application, the formulations present in commercial form are, if appropriate, diluted in a customary manner, for example in the case of wettable powders, emulsifiable concentrates, dispersions and water-dispersible granules with water. Preparations in the form of dusts, granules for soil application or granules for broadcasting and sprayable solutions are not usually diluted with other inert substances prior to application.

The active compounds can be applied to the plants, plant parts, seed or area under cultivation (soil), preferably on the green plants and plant parts, and optionally additionally to the soil.

One possible use is the joint application of the active compounds in the form of tank mixes, where the optimally formulated concentrated formulations of the individual active compounds are, together, mixed in a tank with water, and the spray liquor obtained is applied.

A joint herbicidal formulation of the active compounds (A) and (B) has the advantage that it can be applied more easily since the quantities of the components are already adjusted to the correct ratio to one another. Moreover, the auxiliaries in the formulation can be adjusted optimally to one another, whereas a tank mix of different formulations may result in unwanted combinations of auxiliaries.

A. GENERAL FORMULATION EXAMPLES a) A dust is obtained by mixing 10 parts by weight of an active compound/active compound mixture and 90 parts by weight of talc as inert substance and comminuting the mixture in a hammer mill.

b) A wettable powder which is readily dispersible in water is obtained by mixing 25 parts by weight of an active compound/active compound mixture, 64 parts by weight of kaolin-containing quartz as inert substance, 10 parts by weight of potassium lignosulphonate and 1 part by weight of sodium oleoylmethyltaurinate as wetting agent and dispersant, and grinding the mixture in a pinned-disc mill.

c) A dispersion concentrate which is readily dispersible in water is obtained by mixing 20 parts by weight of an active compound/active compound mixture with 6 parts by weight of alkylphenol polyglycol ether (Triton® X 207), 3 parts by weight of isotridecanol polyglycol ether (8 EO) and 71 parts by weight of paraffinic mineral oil (boiling range for example approximately 255 to 277° C.) and grinding the mixture in a ball mill to a fineness of below 5 microns.

d) An emulsifiable concentrate is obtained from 15 parts by weight of an active compound/active compound mixture, 75 parts by weight of cyclohexanone as solvent and 10 parts by weight of ethoxylated nonylphenol as emulsifier.

e) Water-dispersible granules are obtained by mixing
   75 parts by weight of an active compound/active compound mixture,
   10 parts by weight of calcium lignosulphonate,
   5 parts by weight of sodium lauryl sulphate,
   3 parts by weight of polyvinyl alcohol and
   7 parts by weight of kaolin,
   grinding the mixture in a pinned-disc mill, and granulating the powder in a fluidized bed by spray application of water as a granulating liquid.

f) Water-dispersible granules are also obtained by homogenizing and precomminuting
   25 parts by weight of an active compound/active compound mixture,
   5 parts by weight of sodium 2,2'-dinaphthylmethane-6,6'-disulphonate,
   2 parts by weight of sodium oleoylmethyltaurinate,
   1 part by weight of polyvinyl alcohol,
   17 parts by weight of calcium carbonate and
   50 parts by weight of water
   on a colloid mill, subsequently grinding the mixture in a bead mill and atomizing and drying the resulting suspension in a spray tower by means of a single-substance nozzle.

WORKING EXAMPLES

Greenhouse Experiments

In standard practice of the experiment, seeds of various broad-leaved weed and weed grass biotypes (origins) having various resistance mechanisms to various mechanisms of action were sown in a pot which had a diameter of 8-13 cm and was filled with natural soil of a standard field soil (loamy silt; not sterile) or a 1:1 mixture of the standard field soil (loamy silt; not sterile) and standard soil type ED73 and covered with a covering layer of the soil or a layer of sand of about 1 cm, alternatively sown in a soil-filled planting dish and, after germination, pricked out into soil-filled pots and covered. The 1:1 mixture of the two soil types was used specifically for cultivating small-seeded dicotyledonous weed since the standard field soil on its own tends to silt up, which may have an adverse effect on the emergence of small-seeded weeds. The resistances mentioned in the tables were confirmed beforehand in standard monitoring experiments. Nevertheless, the origins examined may have additional, hitherto unconfirmed resistances to various mechanisms of action.

The pots were then cultivated in a greenhouse (12-16 h light, temperature day 20-22° C., night 15-18° C.) until the time of application. The pots were treated at various BBCH stages of the seeds/plants on a laboratory track sprayer with spray liquors comprising the compositions according to the invention, mixtures of the prior art or the individual components. Application of the active compounds or active compound combinations and wetting agents formulated as WG, WP, EC or otherwise was carried out at the appropriate growth stages of the plants. The amount of water used for spray application was 100-600 l/ha. After the treatment, the plants were returned to the greenhouses and fertilized and watered as required. The pots were cultivated in a greenhouse (12-16 h light, temperature day 20-22° C., night 15-18° C.).

3 weeks after the application, the foliar effect was evaluated on a scale of 0-100%:
0%=no noticeable effect compared to untreated plants
100%=full effect compared to untreated plants The following abbreviations were used:
BBCH the BBCH code provides information about the morphological development stage of a plant. Officially, the abbreviation denotes the Biologische Bundesanstalt, Bundessortenamt and CHemische Industrie [Federal Biological Institute for Agriculture and Forestry, Federal Office for Crop Plant Varieties, Chemical Industry]. The range of BBCH 00-10 denotes the germination stages of the seeds until surface penetration. The range of BBCH 11-25 denotes the leaf development stages until stocking (corresponds to the number of tillers or side-shoots).
PE pre-emergence soil application; BBCH of the seeds/plants 00-10
PO post-emergence application on the green parts of the plants; BBCH of the plants 11-25
IU soil loamy silt—standard field soil
l/ha liters per hectare
S sensitive—the weed populations are sensitive to the active compounds tested
TSR target-site resistance. The weed populations comprise biotypes having a site-of-action-specific resistance, i.e. the binding site at the site of action is modified as a result of natural mutations in the gene sequence so that the active compounds are no longer able to bind, or bind in an unsatisfactory manner, and are therefore no longer able to act.
NTR non-target-site herbicide resistance; this is differentiated, inter alia, into EMR (Enhanced Metabolic Resistance) (the weed populations comprise biotypes having metabolic resistance, i.e. the plants are capable of metabolizing the active compounds more quickly via enzyme complexes, i.e. the active compounds are degraded more quickly in the plant), into reduced penetration into the plant, reduced translocation in the plant, accelerated excretion. In some biotypes, the EMR mechanism was demonstrated biochemically directly. In other cases, where TSR could not be demonstrated, NTR is assumed.
NA not analysed.
R the weed populations comprise biotypes having resistance to individual active compounds and/or mechanisms of action, i.e. the plants are capable of surviving, by various mechanisms (not investigated any further), application of the active compounds, and of reproducing.
HRAC Herbicide Resistance Action Committee. Committee of the research-conducting industries, which classifies the approved active compounds according to their mode of action (e.g. HRAC group B=acetolactate synthase inhibitors (ALS)).

HRAC group A=acetyl coenzyme A carboxylase inhibitors (ACCase).
HRAC group B=acetolactate synthase inhibitors (ALS).
HRAC group C1=photosystem I inhibitors (PSI).
HRAC group C2=photosystem II inhibitors (PSII).
HRAC group G=inhibitors of EPSP-glyphosate.
HRAC group K1=inhibitors of microtubuli arrangement.
HRAC group K3=inhibitors of cell division.
HRAC group L=inhibitors of cellulose biosynthesis-indaziflam.
dosage g of AS/ha=application rate in grams of active substance per hectare.
AS=active substance (based on 100% of active ingredient)=a.i.
ALOMY=*Alopecurus myosuroides*
AMAPA=*Amaranthus palmeri*
AMATA=*Amaranthus rudis*
APESV=*Apera spica-venti*
BIDSU=*Bidens subalternans*
BRODI=*Bromus diformis*
CHEAL=*Chenopodium album*
EPHHL=*Euphorbia heterophylla*
ERIBO=*Erigeron bonariensis*
ERICA=*Erigeron canadensis*
KCHSC=*Kochia scoparia*
LOLMU=*Lolium multiflorum*
LOLRI=*Lolium rigidum*
LOLSS=*Lolium* spp.

The herbicidal effects of the compositions were determined by comparison with active compounds applied individually against economically important mono- and dicotyledonous harmful plants. The synergistic herbicidal effects were calculated using Colby's formula (cf. S. R. Colby; Weeds 15 (1967), 20-22):

$$E = A + B - (A \times B)/100$$

where:
A, B=the respective effect of component A or B in percent at a dosage of a or b grams of AS/ha;
$E^C$=expected value according to Colby in % at a dosage of a+b grams of AS/ha.

Δ=difference (%) between the measured value—%—and the expected value—%—(measured value minus expected value)
$\Delta^D$=difference (%) between the measured value of an observation A—%—and the measured value of an observation B—%. The observed values A and B can vary according to the experimental approach and are defined in the Results section (e.g. ratio: A=PE application onto the soil, to B=mixing into the soil; or A=PE application onto the soil, to B=pre-sowing application onto the soil etc.).

Evaluation:
  measured values: in each case for (A), (B) and (A)+(B) in %
Evaluation:
  measured value (%) greater > than $E^C$: ≙ synergism (+Δ)
  measured value (%) equal to = $E^C$: ≙ additive effect (±0Δ)
  measured value (%) smaller < than $E^C$: ≙ antagonism (−Δ)

Here, the herbicidal effects of the compositions according to the invention exceeded the expected values calculated using Colby's formula.

Evaluations gave the results listed in Tables 1-3 which clearly show a synergistic effect on individual biotypes.

Unless mentioned otherwise, indaziflam (A) was applied as SC500 (suspension concentrate) corresponding to 500 g of active substance per liter of formulation product. Application of the active compounds of group (B) was as follows.
flazasulfuron (B1) as WG25 (wettable granule) formulation,
foramsulfuron (B2) as WG50 formulation,
rimsulfuron (B3) as WG25 formulation,
chlorimuron-ethyl (B4) as WG25 formulation,
thiencarbazone-methyl (B5) as WP10 (wettable powder) formulation.

In the post-emergence tests (PO), an additive (adjuvant) was added to the individual active compounds and mixtures thereof for better wetting. The additive in question was an alkyl ether sulphate (Genapol LRO) at an application rate of 1 l/ha, corresponding to 276.5 g of active substance per ha. On its own, this additive has no effect on the plants, and it serves, as already mentioned, to improve wetting.

TABLE 1

Comparison of the effect of the mixture on resistant biotypes following PO application according to the test method described a

| Active compounds | Dose g of AS/ha | KCHSC sensitive | KCHSC resistant - group B (TSR) | BRODI sensitive | BRODI resistant - group A (TSR), B (NTR) and G (NTR) | BIDSU sensitive | BIDSU resistant - group B (TSR) | BIDSU resistant - group B (TSR) |
|---|---|---|---|---|---|---|---|---|
| (A) | 50 | 30 | 30 | 70 | 65 | 40 | 40 | 40 |
| (B6) | 20 | 90 | 0 | 90 | 70 | 60 | 10 | 10 |
| (A) + (B6) | 50 + 20 | 100 | 70 | 100 | 100 | 90 | 80 | 88 |
| | | $E^c$ = 93; Δ +7 | $E^c$ = 30; Δ +40 | $E^c$ = 97; Δ +3 | $E^c$ = 90; Δ +10 | $E^c$ = 76; Δ +14 | $E^c$ = 46; Δ +34 | $E^c$ = 46; Δ +42 |
| (A) | 50 | 30 | 30 | 70 | 65 | 40 | 40 | 40 |
| (B4) | 20 | 90 | 0 | 100 | 70 | 60 | 20 | 20 |
| (A) + (B4) | 50 + 20 | 100 | 95 | 100 | 100 | 85 | 90 | 70 |
| | | $E^c$ = 93; Δ +7 | $E^c$ = 30; Δ +65 | $E^c$ = 100; Δ ±0 | $E^c$ = 90; Δ +10 | $E^c$ = 76; Δ +9 | $E^c$ = 52; Δ +38 | $E^c$ = 52; Δ +18 |
| (A) | 50 | 30 | 30 | 70 | 65 | 40 | 40 | 40 |
| (B1) | 20 | 90 | 0 | 100 | 75 | 70 | 30 | 30 |
| (A) + (B1) | 50 + 20 | 95 | 75 | 100 | 100 | 95 | 95 | 75 |
| | | $E^c$ = 93; Δ +2 | $E^c$ = 30; Δ +45 | $E^c$ = 100; Δ ±0 | $E^c$ = 91; Δ +9 | $E^c$ = 82; Δ +13 | $E^c$ = 58; Δ +37 | $E^c$ = 58; Δ +17 |

TABLE 1-continued

Comparison of the effect of the mixture on resistant biotypes following PO application according to the test method described

| | | | | | | | | |
|---|---|---|---|---|---|---|---|---|
| (A) | 50 | 30 | 30 | 70 | 65 | 40 | 40 | 40 |
| (B3) | 20 | 90 | 0 | 100 | 75 | 70 | 60 | 10 |
| (A) + (B3) | 50 + 20 | 100 | 75 | 100 | 100 | 95 | 80 | 75 |
| | | $E^c$ = 93; | $E^c$ = 30; | $E^c$ = 100; | $E^c$ = 91; | $E^c$ = 82; | $E^c$ = 76; | $E^c$ = 46; |
| | | Δ +7 | Δ +45 | Δ ±0 | Δ +9 | Δ +13 | Δ +4 | Δ +29 |
| (A) | 50 | 30 | 30 | 70 | 65 | 40 | 40 | 40 |
| (B2) | 20 | 90 | 0 | 100 | 75 | 30 | 0 | 0 |
| (A) + (B2) | 50 + 20 | 100 | 88 | 100 | 100 | 90 | 90 | 75 |
| | | $E^c$ = 93; | $E^c$ = 30; | $E^c$ = 100; | $E^c$ = 91; | $E^c$ = 58; | $E^c$ = 40; | $E^c$ = 40; |
| | | Δ +7 | Δ +58 | Δ ±0 | Δ +9 | Δ +32 | Δ +50 | Δ +35 |
| (A) | 50 | 30 | 30 | 70 | 65 | 40 | 40 | 40 |
| (B5) | 20 | 90 | 0 | 95 | 50 | 60 | 0 | 0 |
| (A) + (B5) | 50 + 20 | 100 | 90 | 100 | 100 | 90 | 100 | 70 |
| | | $E^c$ = 93; | $E^c$ = 30; | $E^c$ = 99; | $E^c$ = 83; | $E^c$ = 76; | $E^c$ = 40; | $E^c$ = 40; |
| | | Δ +7 | Δ +60 | Δ +2 | Δ +18 | Δ +14 | Δ +60 | Δ +30 | b

| Active compounds | Dose g of AS/ha | AMATA sensitive | AMATA resistant - group B (TSR), C1 (TSR) | AMAPA resistant - group B (TSR), C1 (TSR) and G (NTR) | EPHHL sensitive | EPHHL resistant - group B (TSR) and G (NTR) | EPHHL resistant - group B (TSR) | APESV sensitive | APESV resistant - group B (TSR, NTR) and K1/3 (NA) |
|---|---|---|---|---|---|---|---|---|---|
| (A) | 50 | 50 | 40 | 50 | 60 | 50 | 55 | 65 | 60 |
| (B6) | 20 | 50 | 70 | 60 | 90 | 60 | 70 | 100 | 10 |
| (A) + (B6) | 50 + 20 | 90 | 100 | 100 | 100 | 100 | 100 | 100 | 100 |
| | | $E^c$ = 75; | $E^c$ = 82; | $E^c$ = 80; | $E^c$ = 96; | $E^c$ = 80; | $E^c$ = 87; | $E^c$ = 100; | $E^c$ = 64; |
| | | Δ +15 | Δ +18 | Δ +20 | Δ +4 | Δ +20 | Δ +14 | Δ ±0 | Δ +36 |
| (A) | 50 | 50 | 40 | 50 | 60 | 50 | 55 | 65 | 60 |
| (B4) | 20 | 30 | 60 | 30 | 60 | 30 | 30 | 100 | 0 |
| (A) + (B4) | 50 + 20 | 83 | 100 | 100 | 100 | 80 | 100 | 100 | 100 |
| | | $E^c$ = 65; | $E^c$ = 76; | $E^c$ = 65; | $E^c$ = 84; | $E^c$ = 65; | $E^c$ = 69; | $E^c$ = 100; | $E^c$ = 60; |
| | | Δ +18 | Δ +24 | Δ +35 | Δ +16 | Δ +15 | Δ +32 | Δ ±0 | Δ +40 |
| (A) | 50 | 50 | 40 | 50 | 60 | 50 | 55 | 65 | 60 |
| (B1) | 20 | 60 | 50 | 40 | 80 | 40 | 30 | 100 | 30 |
| (A) + (B1) | 50 + 20 | 90 | 100 | 100 | 100 | 89 | 100 | 100 | 100 |
| | | $E^c$ = 80; | $E^c$ = 70; | $E^c$ = 70; | $E^c$ = 92; | $E^c$ = 70; | $E^c$ = 69; | $E^c$ = 100; | $E^c$ = 72; |
| | | Δ +10 | Δ +30 | Δ +30 | Δ +8 | Δ +19 | Δ +32 | Δ ±0 | Δ +28 |
| (A) | 50 | 50 | 40 | 50 | 60 | 50 | 55 | 65 | 60 |
| (B3) | 20 | 70 | 90 | 70 | 80 | 50 | 60 | 100 | 20 |
| (A) + (B3) | 50 + 20 | 95 | 100 | 100 | 95 | 95 | 98 | 100 | 100 |
| | | $E^c$ = 85; | $E^c$ = 94; | $E^c$ = 85; | $E^c$ = 92; | $E^c$ = 75; | $E^c$ = 82; | $E^c$ = 100; | $E^c$ = 68; |
| | | Δ +10 | Δ +6 | Δ +15 | Δ +3 | Δ +20 | Δ +16 | Δ ±0 | Δ +32 |
| (A) | 50 | 50 | 40 | 50 | 60 | 50 | 55 | 65 | 60 |
| (B2) | 20 | 40 | 90 | 40 | 80 | 40 | 30 | 100 | 0 |
| (A) + (B2) | 50 + 20 | 85 | 100 | 100 | 98 | 93 | 100 | 100 | 100 |
| | | $E^c$ = 70; | $E^c$ = 94; | $E^c$ = 70; | $E^c$ = 92; | $E^c$ = 70; | $E^c$ = 69; | $E^c$ = 100; | $E^c$ = 60; |
| | | Δ +15 | Δ +6 | Δ +30 | Δ +6 | Δ +23 | Δ +32 | Δ ±0 | Δ +40 |
| (A) | 50 | 50 | 40 | 50 | 60 | 50 | 55 | 65 | 60 |
| (B5) | 20 | 30 | 40 | 0 | 70 | 30 | 20 | 100 | 0 |
| (A) + (B5) | 50 + 20 | 90 | 100 | 80 | 100 | 95 | 100 | 100 | 100 |
| | | $E^c$ = 65; | $E^c$ = 64; | $E^c$ = 50; | $E^c$ = 88; | $E^c$ = 65; | $E^c$ = 64; | $E^c$ = 100; | $E^c$ = 60; |
| | | Δ +25 | Δ +36 | Δ +30 | Δ +12 | Δ +30 | Δ +36 | Δ ±0 | Δ +40 | c

| Active compounds | Dose g of AS/ha | ALOMY sensitive | ALOMY resistant - group A (TSR, NTR), B (TSR, NTR) and C2 (NA) | ALOMY resistant - group A (TSR, NTR), B (TSR, NTR) and C2 (NA) | LOLSS sensitive | LOLSS resistant group A (TSR, NTR), B (NTR) and C2 (NA) | LOLSS resistant - group G (NTR) | LOLSS resistant group A (TSR, NTR), B (TSR, NTR) and C2 (NA) |
|---|---|---|---|---|---|---|---|---|
| (A) | 50 | 75 | 60 | 60 | 75 | 60 | 65 | 60 |
| (B6) | 20 | 100 | 20 | 20 | 90 | 65 | 65 | 10 |
| (A) + (B6) | 50 + 20 | 100 | 100 | 100 | 100 | 100 | 100 | 100 |
| | | $E^c$ = 100; | $E^c$ = 68; | $E^c$ = 68; | $E^c$ = 98; | $E^c$ = 86; | $E^c$ = 88; | $E^c$ = 64; |
| | | Δ ±0 | Δ +32 | Δ +32 | Δ +3 | Δ +14 | Δ +12 | Δ +36 |
| (A) | 50 | 75 | 60 | 60 | 75 | 60 | 65 | 60 |
| (B4) | 20 | 100 | 0 | 0 | 35 | 55 | 50 | 0 |
| (A) + (B4) | 50 + 20 | 100 | 100 | 100 | 100 | 100 | 100 | 100 |
| | | $E^c$ = 100; | $E^c$ = 60; | $E^c$ = 60; | $E^C$ = 84 | $E^c$ = 82; | $E^c$ = 83; | $E^c$ = 60; |
| | | Δ ±0 | Δ +40 | Δ +40 | Δ +16 | Δ +18 | Δ +18 | Δ +40 |

TABLE 1-continued

Comparison of the effect of the mixture on resistant biotypes following PO application according to the test method described

| (A)       | 50      | 75          | 60          | 60          | 75          | 60          | 65          | 60          |
|-----------|---------|-------------|-------------|-------------|-------------|-------------|-------------|-------------|
| (B1)      | 20      | 100         | 30          | 10          | 95          | 60          | 60          | 30          |
| (A) + (B1)| 50 + 20 | 100         | 100         | 100         | 100         | 100         | 100         | 100         |
|           |         | $E^c = 100$; | $E^c = 72$; | $E^c = 64$; | $E^c = 99$; | $E^c = 84$; | $E^c = 86$; | $E^c = 72$; |
|           |         | Δ ±0        | Δ +28       | Δ +36       | Δ +1        | Δ +16       | Δ +14       | Δ +28       |
| (A)       | 50      | 75          | 60          | 60          | 75          | 60          | 65          | 60          |
| (B3)      | 20      | 100         | 10          | 10          | 95          | 60          | 60          | 15          |
| (A) + (B3)| 50 + 20 | 100         | 100         | 100         | 100         | 100         | 100         | 100         |
|           |         | $E^c = 100$; | $E^c = 64$; | $E^c = 64$; | $E^c = 99$; | $E^c = 84$; | $E^c = 86$; | $E^c = 66$; |
|           |         | Δ ±0        | Δ +36       | Δ +36       | Δ +1        | Δ +16       | Δ +14       | Δ +34       |
| (A)       | 50      | 75          | 60          | 60          | 75          | 60          | 65          | 60          |
| (B2)      | 20      | 100         | 10          | 0           | 100         | 60          | 50          | 40          |
| (A) + (B2)| 50 + 20 | 100         | 100         | 100         | 100         | 100         | 100         | 100         |
|           |         | $E^c = 100$; | $E^c = 64$; | $E^c = 60$; | $E^c = 100$; | $E^c = 84$; | $E^c = 83$; | $E^c = 76$; |
|           |         | Δ ±0        | Δ +36       | Δ +40       | Δ ±0        | Δ +16       | Δ +18       | Δ +24       |
| (A)       | 50      | 75          | 60          | 60          | 75          | 60          | 65          | 60          |
| (B5)      | 20      | 100         | 0           | 0           | 85          | 50          | 40          | 0           |
| (A) + (B5)| 50 + 20 | 100         | 100         | 100         | 100         | 100         | 100         | 100         |
|           |         | $E^c = 100$; | $E^c = 60$; | $E^c = 60$; | $E^c = 96$; | $E^c = 80$; | $E^c = 79$; | $E^c = 60$; |
|           |         | Δ ±0        | Δ +40       | Δ +40       | Δ +4        | Δ +20       | Δ +21       | Δ +40       | d

| Active compounds | Dose g of AS/ha | CHEAL sensitive | CHEAL resistant -group B (TSR), C1 (NA) and G (NTR) | ERICA sensitive | ERICA resistant - group B (NA) and G (NTR) | ERIBO sensitive | ERIBO resistant - group B (NA) and G (NTR) |
|---|---|---|---|---|---|---|---|
| (A)       | 50      | 70         | 70         | 50         | 50         | 50         | 50         |
| (B6)      | 20      | 90         | 80         | 90         | 60         | 90         | 60         |
| (A) + (B6)| 50 + 20 | 100        | 100        | 100        | 90         | 100        | 90         |
|           |         | $E^c = 97$; | $E^c = 94$; | $E^c = 95$; | $E^c = 80$; | $E^c = 95$; | $E^c = 80$; |
|           |         | Δ +3       | Δ +6       | Δ +5       | Δ +10      | Δ +5       | Δ +10      |
| (A)       | 50      | 70         | 70         | 50         | 50         | 50         | 50         |
| (B4)      | 20      | 60         | 50         | 80         | 60         | 80         | 60         |
| (A) + (B4)| 50 + 20 | 100        | 95         | 95         | 90         | 95         | 90         |
|           |         | $E^c = 88$; | $E^c = 85$; | $E^c = 90$; | $E^c = 80$; | $E^c = 90$; | $E^c = 80$; |
|           |         | Δ +12      | Δ +10      | Δ +5       | Δ +10      | Δ +5       | Δ +10      |
| (A)       | 50      | 70         | 70         | 50         | 50         | 50         | 50         |
| (B1)      | 20      | 80         | 70         | 90         | 50         | 90         | 50         |
| (A) + (B1)| 50 + 20 | 100        | 100        | 100        | 98         | 100        | 98         |
|           |         | $E^c = 94$; | $E^c = 91$; | $E^c = 95$; | $E^c = 75$; | $E^c = 95$; | $E^c = 75$; |
|           |         | Δ +6       | Δ +9       | Δ +5       | Δ +23      | Δ +5       | Δ +23      |
| (A)       | 50      | 70         | 70         | 50         | 50         | 50         | 50         |
| (B3)      | 20      | 80         | 70         | 90         | 60         | 90         | 60         |
| (A) + (B3)| 50 + 20 | 100        | 100        | 100        | 95         | 100        | 95         |
|           |         | $E^c = 94$; | $E^c = 91$; | $E^c = 95$; | $E^c = 80$; | $E^c = 95$; | $E^c = 80$; |
|           |         | Δ +6       | Δ +9       | Δ +5       | Δ +15      | Δ +5       | Δ +15      |
| (A)       | 50      | 70         | 70         | 50         | 50         | 50         | 50         |
| (B2)      | 20      | 70         | 70         | 50         | 40         | 50         | 40         |
| (A) + (B2)| 50 + 20 | 100        | 95         | 100        | 90         | 100        | 90         |
|           |         | $E^c = 91$; | $E^c = 91$; | $E^c = 75$; | $E^c = 70$; | $E^c = 75$; | $E^c = 70$; |
|           |         | Δ +92      | Δ +9       | Δ +25      | Δ +20      | Δ +25      | Δ +20      |
| (A)       | 50      | 70         | 70         | 50         | 50         | 50         | 50         |
| (B5)      | 20      | 70         | 70         | 70         | 60         | 70         | 60         |
| (A) + (B5)| 50 + 20 | 100        | 100        | 100        | 95         | 100        | 95         |
|           |         | $E^c = 91$; | $E^c = 91$; | $E^c = 85$; | $E^c = 80$; | $E^c = 85$; | $E^c = 80$; |
|           |         | Δ +9       | Δ +9       | Δ +15      | Δ +15      | Δ +15      | Δ +15      |

TABLE 2

Comparison of the effect of the mixture on resistant biotypes following PE application according to the test method described a

| Active compounds | Dose g of AS/ha | KCHSC sensitive | KCHSC resistant - group B (TSR) | BRODI sensitive | BRODI resistant - group A (TSR), B (NTR) and G (NTR) | BIDSU sensitive | BIDSU resistant - group B (TSR) | BIDSU resistant - group B (TSR) |
|---|---|---|---|---|---|---|---|---|
| (A)       | 12.5      | 40         | 40         | 75         | 70         | 50         | 50         | 50         |
| (B6)      | 20        | 30         | 0          | 90         | 90         | 70         | 40         | 0          |
| (A) + (B6)| 12.5 + 20 | 90         | 70         | 100        | 100        | 98         | 98         | 98         |
|           |           | $E^c = 58$; | $E^c = 40$; | $E^c = 98$; | $E^c = 97$; | $E^c = 85$; | $E^c = 70$; | $E^c = 50$; |
|           |           | Δ +32      | Δ +30      | Δ +3       | Δ +3       | Δ +13      | Δ +28      | Δ +48      |

TABLE 2-continued

Comparison of the effect of the mixture on resistant biotypes following PE application according to the test method described

| (A)       | 12.5      | 40           | 40           | 75           | 70           | 50           | 50           | 50           |
|-----------|-----------|--------------|--------------|--------------|--------------|--------------|--------------|--------------|
| (B4)      | 20        | 50           | 0            | 95           | 80           | 90           | 50           | 0            |
| (A) + (B4)| 12.5 + 20 | 90           | 75           | 100          | 100          | 90           | 98           | 70           |
|           |           | $E^c = 70$;  | $E^c = 40$;  | $E^c = 99$;  | $E^c = 94$;  | $E^c = 95$;  | $E^c = 75$;  | $E^c = 50$;  |
|           |           | $\Delta$ +20 | $\Delta$ +35 | $\Delta$ +1  | $\Delta$ +6  | $\Delta$ -5  | $\Delta$ +23 | $\Delta$ +20 |
| (A)       | 12.5      | 40           | 40           | 75           | 70           | 50           | 50           | 50           |
| (B1)      | 20        | 70           | 0            | 80           | 70           | 80           | 40           | 0            |
| (A) + (B1)| 12.5 + 20 | 95           | 50           | 100          | 100          | 95           | 98           | 100          |
|           |           | $E^c = 82$;  | $E^c = 40$;  | $E^c = 95$;  | $E^c = 91$;  | $E^c = 90$;  | $E^c = 70$;  | $E^c = 50$;  |
|           |           | $\Delta$ +13 | $\Delta$ +10 | $\Delta$ +5  | $\Delta$ +9  | $\Delta$ +5  | $\Delta$ +28 | $\Delta$ +50 |
| (A)       | 12.5      | 40           | 40           | 75           | 70           | 50           | 50           | 50           |
| (B3)      | 20        | 80           | 20           | 80           | 70           | 80           | 30           | 0            |
| (A) + (B3)| 12.5 + 20 | 80           | 20           | 100          | 100          | 85           | 75           | 50           |
|           |           | $E^c = 84$;  | $E^c = 40$;  | $E^c = 95$;  | $E^c = 91$;  | $E^c = 90$;  | $E^c = 65$;  | $E^c = 50$;  |
|           |           | $\Delta$ -4  | $\Delta$ -20 | $\Delta$ +5  | $\Delta$ +9  | $\Delta$ -5  | $\Delta$ +10 | $\Delta$ ±0  |
| (A)       | 12.5      | 40           | 40           | 75           | 70           | 50           | 50           | 50           |
| (B2)      | 20        | 60           | 0            | 75           | 70           | 30           | 30           | 0            |
| (A) + (B2)| 12.5 + 20 | 60           | 40           | 100          | 100          | 50           | 95           | 60           |
|           |           | $E^c = 76$;  | $E^c = 40$;  | $E^c = 94$;  | $E^c = 91$;  | $E^c = 65$;  | $E^c = 65$;  | $E^c = 50$;  |
|           |           | $\Delta$ -16 | $\Delta$ ±0  | $\Delta$ +6  | $\Delta$ +9  | $\Delta$ -15 | $\Delta$ +30 | $\Delta$ +10 |
| (A)       | 12.5      | 40           | 40           | 75           | 70           | 50           | 50           | 50           |
| (B5)      | 20        | 85           | 0            | 70           | 70           | 75           | 50           | 0            |
| (A) + (B5)| 12.5 + 20 | 95           | 50           | 100          | 100          | 60           | 85           | 70           |
|           |           | $E^c = 91$;  | $E^c = 40$;  | $E^c = 93$;  | $E^c = 91$;  | $E^c = 80$;  | $E^c = 75$;  | $E^c = 50$;  |
|           |           | $\Delta$ +4  | $\Delta$ +10 | $\Delta$ +8  | $\Delta$ +9  | $\Delta$ -20 | $\Delta$ +10 | $\Delta$ +20 | b

| Active compounds | Dose g of AS/ha | AMATA sensitive | AMATA resistant - group B (TSR), C1 (TSR) | EPHHL sensitive | EPHHL resistant - group B (TSR) and G (NTR) | EPHHL resistant - group B (TSR) | APESV sensitive | APESV resistant - group B (TSR, NTR) and K1/3 (NA) |
|---|---|---|---|---|---|---|---|---|
| (A) | 12.5 | 70 | 70 | 50 | 0 | 0 | 90 | 70 |
| (B) AE 1801486 | 20 | 60 | 40 | 20 | 20 | 0 | 89 | 50 |
| (A) + (B) | 12.5 + 20 | 100 | 100 | 95 | 70 | 100 | 100 | 100 |
|  |  | $E^c = 88$; | $E^c = 82$; | $E^c = 60$; | $E^c = 20$; | $E^c = 0$; | $E^c = 99$; | $E^c = 85$; |
|  |  | $\Delta$ +12 | $\Delta$ +18 | $\Delta$ +35 | $\Delta$ +50 | $\Delta$ +100 | $\Delta$ +1 | $\Delta$ +15 |
| (A) | 12.5 | 70 | 70 | 50 | 0 | 0 | 90 | 70 |
| (B4) | 20 | 60 | 50 | 60 | 40 | 0 | 90 | 40 |
| (A) + (B4) | 12.5 + 20 | 100 | 100 | 95 | 80 | 50 | 100 | 100 |
|  |  | $E^c = 88$; | $E^c = 85$; | $E^c = 80$; | $E^c = 40$; | $E^c = 0$; | $E^c = 99$; | $E^c = 82$; |
|  |  | $\Delta$ +12 | $\Delta$ +15 | $\Delta$ +15 | $\Delta$ +40 | $\Delta$ +50 | $\Delta$ +1 | $\Delta$ +18 |
| (A) | 12.5 | 70 | 70 | 50 | 0 | 0 | 90 | 70 |
| (B1) | 20 | 70 | 60 | 40 | 20 | 0 | 85 | 40 |
| (A) + (B1) | 12.5 + 20 | 100 | 100 | 95 | 70 | 60 | 100 | 100 |
|  |  | $E^c = 91$; | $E^c = 88$; | $E^c = 70$; | $E^c = 20$; | $E^c = 0$; | $E^c = 99$; | $E^c = 82$; |
|  |  | $\Delta$ +9 | $\Delta$ +12 | $\Delta$ +25 | $\Delta$ +50 | $\Delta$ +60 | $\Delta$ +2 | $\Delta$ +18 |
| (A) | 12.5 | 70 | 70 | 50 | 0 | 0 | 90 | 70 |
| (B3) | 20 | 70 | 60 | 30 | 0 | 0 | 93 | 35 |
| (A) + (B3) | 12.5 + 20 | 100 | 100 | 75 | 40 | 100 | 100 | 100 |
|  |  | $E^c = 91$; | $E^c = 88$; | $E^c = 65$; | $E^c = 0$; | $E^c = 0$; | $E^c = 99$; | $E^c = 81$; |
|  |  | $\Delta$ +9 | $\Delta$ +12 | $\Delta$ +10 | $\Delta$ +40 | $\Delta$ +100 | $\Delta$ +1 | $\Delta$ +20 |
| (A) | 12.5 | 70 | 70 | 50 | 0 | 0 | 90 | 70 |
| (B2) | 20 | 60 | 40 | 30 | 0 | 0 | 95 | 20 |
| (A) + (B2) | 12.5 + 20 | 100 | 100 | 70 | 40 | 30 | 100 | 100 |
|  |  | $E^c = 88$; | $E^c = 82$; | $E^c = 65$; | $E^c = 0$; | $E^c = 0$; | $E^c = 100$; | $E^c = 76$; |
|  |  | $\Delta$ +12 | $\Delta$ +18 | $\Delta$ +5 | $\Delta$ +40 | $\Delta$ +30 | $\Delta$ +1 | $\Delta$ +24 |
| (A) | 12.5 | 70 | 70 | 50 | 0 | 0 | 90 | 70 |
| (B5) | 20 | 60 | 40 | 30 | 0 | 0 | 95 | 20 |
| (A) + (B5) | 12.5 + 20 | 90 | 100 | 85 | 20 | 30 | 100 | 100 |
|  |  | $E^c = 88$; | $E^c = 82$; | $E^c = 65$; | $E^c = 0$; | $E^c = 0$; | $E^c = 100$; | $E^c = 76$; |
|  |  | $\Delta$ +2 | $\Delta$ +18 | $\Delta$ +20 | $\Delta$ +20 | $\Delta$ +30 | $\Delta$ +1 | $\Delta$ +24 |

TABLE 2-continued

Comparison of the effect of the mixture on resistant biotypes following PE application according to the test method described c

| Active compounds | Dose g of AS/ha | ALOMY sensitive | ALOMY resistant - group A (TSR, NTR), B (TSR, NTR) and C2 (NA) | ALOMY resistant - group A (TSR, NTR), B (TSR, NTR) and C2 (NA) | LOLSS sensitive | LOLSS resistant group A (TSR, NTR), B (NTR) and C2 (NA) | LOLSS resistant - group G (NTR) | LOLSS resistant group A (TSR, NTR), B (TSR, NTR) and C2 (NA) |
|---|---|---|---|---|---|---|---|---|
| (A) | 12.5 | 85 | 65 | 60 | 80 | 50 | 75 | 50 |
| (B6) | 20 | 100 | 30 | 15 | 88 | 88 | 90 | 88 |
| (A) + (B6) | 12.5 + 20 | 100 | 100 | 100 | 100 | 100 | 100 | 100 |
| | | $E^c = 100$; $\Delta \pm 0$ | $E^c = 76$; $\Delta +25$ | $E^c = 66$; $\Delta +34$ | $E^c = 98$; $\Delta +2$ | $E^c = 94$; $\Delta +6$ | $E^c = 98$; $\Delta +3$ | $E^c = 94$; $\Delta +6$ |
| (A) | 12.5 | 85 | 65 | 60 | 80 | 50 | 75 | 50 |
| (B4) | 20 | 100 | 20 | 15 | 70 | 55 | 60 | 10 |
| (A) + (B4) | 12.5 + 20 | 100 | 100 | 100 | 100 | 100 | 100 | 100 |
| | | $E^c = 100$; $\Delta \pm 0$ | $E^c = 72$; $\Delta +28$ | $E^c = 66$; $\Delta +34$ | $E^c = 94$; $\Delta +6$ | $E^c = 78$; $\Delta +23$ | $E^c = 90$; $\Delta +10$ | $E^c = 55$; $\Delta +45$ |
| (A) | 12.5 | 85 | 65 | 60 | 80 | 50 | 75 | 50 |
| (B1) | 20 | 100 | 60 | 10 | 70 | 70 | 80 | 70 |
| (A) + (B1) | 12.5 + 20 | 100 | 100 | 100 | 100 | 100 | 100 | 100 |
| | | $E^c = 100$; $\Delta \pm 0$ | $E^c = 86$; $\Delta +14$ | $E^c = 64$; $\Delta +36$ | $E^c = 94$; $\Delta +6$ | $E^c = 85$; $\Delta +15$ | $E^c = 95$; $\Delta +5$ | $E^c = 85$; $\Delta +15$ |
| (A) | 12.5 | 85 | 65 | 60 | 80 | 50 | 75 | 50 |
| (B3) | 20 | 100 | 30 | 0 | 70 | 50 | 60 | 50 |
| (A) + (B3) | 12.5 + 20 | 100 | 100 | 100 | 100 | 100 | 100 | 100 |
| | | $E^c = 100$; $\Delta \pm 0$ | $E^c = 76$; $\Delta +25$ | $E^c = 60$; $\Delta +40$ | $E^c = 94$; $\Delta +6$ | $E^c = 75$; $\Delta +25$ | $E^c = 90$; $\Delta +10$ | $E^c = 75$; $\Delta +25$ |
| (A) | 12.5 | 85 | 65 | 60 | 80 | 50 | 75 | 50 |
| (B2) | 20 | 90 | 10 | 0 | 78 | 80 | 65 | 60 |
| (A) + (B2) | 12.5 + 20 | 100 | 100 | 100 | 100 | 100 | 100 | 100 |
| | | $E^c = 99$; $\Delta +2$ | $E^c = 69$; $\Delta +32$ | $E^c = 60$; $\Delta +40$ | $E^c = 96$; $\Delta +4$ | $E^c = 90$; $\Delta +10$ | $E^c = 91$; $\Delta +9$ | $E^c = 80$; $\Delta +20$ |
| (A) | 12.5 | 85 | 65 | 60 | 80 | 50 | 75 | 50 |
| (B5) | 20 | 100 | 20 | 0 | 75 | 80 | 70 | 20 |
| (A) + (B5) | 12.5 + 20 | 100 | 100 | 100 | 100 | 100 | 100 | 100 |
| | | $E^c = 100$; $\Delta \pm 0$ | $E^c = 72$; $\Delta +28$ | $E^c = 60$; $\Delta +40$ | $E^c = 95$; $\Delta +5$ | $E^c = 90$; $\Delta +10$ | $E^c = 93$; $\Delta +8$ | $E^c = 60$; $\Delta +40$ | d

| Active compounds | Dose g of AS/ha | CHEAL sensitive | CHEAL resistant - group B (TSR), C1 (NA) and G (NTR) | ERICA sensitive | ERICA resistant - group B (NA) and G (NTR) | ERIBO sensitive | ERIBO resistant - group B (NA) and G (NTR) |
|---|---|---|---|---|---|---|---|
| (A) | 12.5 | 70 | 65 | 70 | 60 | 70 | 60 |
| (B6) | 20 | 90 | 60 | 100 | 0 | 100 | 0 |
| (A) + (B6) | 12.5 + 20 | 100 | 100 | 100 | 100 | 100 | 100 |
| | | $E^c = 97$; $\Delta +3$ | $E^c = 86$; $\Delta +14$ | $E^c = 100$; $\Delta \pm 0$ | $E^c = 60$; $\Delta +40$ | $E^c = 100$; $\Delta \pm 0$ | $E^c = 60$; $\Delta +40$ |
| (A) | 12.5 | 70 | 65 | 70 | 60 | 70 | 60 |
| (B4) | 20 | 90 | 60 | 100 | 0 | 100 | 0 |
| (A) + (B4) | 12.5 + 20 | 100 | 95 | 100 | 100 | 100 | 100 |
| | | $E^c = 97$; $\Delta +3$ | $E^c = 86$; $\Delta +14$ | $E^c = 100$; $\Delta \pm 0$ | $E^c = 60$; $\Delta +40$ | $E^c = 100$; $\Delta \pm 0$ | $E^c = 60$; $\Delta +40$ |
| (A) | 12.5 | 70 | 65 | 70 | 60 | 70 | 60 |
| (B1) | 20 | 88 | 60 | 70 | 0 | 70 | 0 |
| (A) + (B1) | 12.5 + 20 | 100 | 100 | 100 | 100 | 100 | 100 |
| | | $E^c = 96$; $\Delta +4$ | $E^c = 86$; $\Delta +14$ | $E^c = 91$; $\Delta +9$ | $E^c = 60$; $\Delta +40$ | $E^c = 91$; $\Delta +9$ | $E^c = 60$; $\Delta +40$ |
| (A) | 12.5 | 70 | 65 | 70 | 60 | 70 | 60 |
| (B3) | 20 | 85 | 45 | 70 | 0 | 70 | 0 |
| (A) + (B3) | 12.5 + 20 | 100 | 100 | 100 | 100 | 100 | 100 |
| | | $E^c = 96$; $\Delta +5$ | $E^c = 81$; $\Delta +19$ | $E^c = 91$; $\Delta +9$ | $E^c = 60$; $\Delta +40$ | $E^c = 91$; $\Delta +9$ | $E^c = 60$; $\Delta +40$ |
| (A) | 12.5 | 70 | 65 | 70 | 60 | 70 | 60 |
| (B2) | 20 | 80 | 40 | 100 | 0 | 100 | 0 |
| (A) + (B2) | 12.5 + 20 | 100 | 100 | 100 | 100 | 100 | 100 |
| | | $E^c = 94$; $\Delta +6$ | $E^c = 79$; $\Delta +21$ | $E^c = 100$; $\Delta \pm 0$ | $E^c = 60$; $\Delta +40$ | $E^c = 100$; $\Delta \pm 0$ | $E^c = 60$; $\Delta +40$ |

TABLE 2-continued

Comparison of the effect of the mixture on resistant biotypes following PE application according to the test method described

| | | | | | | | |
|---|---|---|---|---|---|---|---|
| (A) | 12.5 | 70 | 65 | 70 | 60 | 70 | 60 |
| (B5) | 20 | 90 | 60 | 60 | 0 | 60 | 0 |
| (A) + (B5) | 12.5 + 20 | 100 | 100 | 100 | 100 | 100 | 100 |
| | | $E^c = 97$; $\Delta +3$ | $E^c = 86$; $\Delta +14$ | $E^c = 88$; $\Delta +12$ | $E^c = 60$; $\Delta +40$ | $E^c = 88$; $\Delta +12$ | $E^c = 60$; $\Delta +40$ |

Table 3a: Comparison of the effect of the mixture on all resistant and sensitive biotypes in PO application

| | Dose g of AS/ha | TTTTT resistant (n = 17) mean | TTTTT sensitive (n = 11) mean | Difference in sensitivities |
|---|---|---|---|---|
| (A) | 50 | 53 | 58 | $\Delta^D - 4$ |
| (B6) | 20 | 44 | 85 | $\Delta^D - 42$ |
| (A) + (B6) | 50 + 20 | 95 | 98 | $\Delta^D - 3$ |
| | | $E^c = 72$; $\Delta + 23$ | $E^c = 93$; $\Delta + 5$ | |
| Average difference $\Delta^D$ of the effect of the individual active compounds (Ø) | | | | $\Delta^D - 23$ |
| Difference $\Delta^D$ between the effect of the mixture and the difference $\Delta^D$ of the average effect of the individual active compounds | | | | $\Delta^D + 20$ |

Table 3b: Comparison of the effect of the mixture on all resistant and sensitive biotypes in PO application

| | Dose g of AS/ha | TTTTT resistant (n = 15) mean | TTTTT sensitive (n = 11) mean | Difference in sensitivities |
|---|---|---|---|---|
| (A) | 50 | 53 | 58 | $\Delta^D - 4$ |
| (B4) | 20 | 31 | 72 | $\Delta^D - 41$ |
| (A) + (B4) | 50 + 20 | 95 | 96 | $\Delta^D - 1$ |
| | | $E^c = 68$; $\Delta + 27$ | $E^c = 88$; $\Delta + 8$ | |
| Average difference $\Delta^D$ of the effect of the individual active compounds (Ø) | | | | $\Delta^D - 22$ |
| Difference $\Delta^D$ between the effect of the mixture and the difference $\Delta^D$ of the average effect of the individual active compounds | | | | $\Delta^D + 21$ |

Table 3c: Comparison of the effect of the mixture on all resistant and sensitive biotypes in PO application

| | Dose g of AS/ha | TTTTT resistant (n = 17) mean | TTTTT sensitive (n = 11) mean | Difference in sensitivities |
|---|---|---|---|---|
| (A) | 50 | 53 | 58 | $\Delta^D - 4$ |
| (B1) | 20 | 40 | 87 | $\Delta^D - 47$ |
| (A) + (B1) | 50 + 20 | 96 | 98 | $\Delta^D - 2$ |
| | | $E^c = 71$; $\Delta + 25$ | $E^c = 94$; $\Delta + 5$ | |
| Average difference $\Delta^D$ of the effect of the individual active compounds (Ø) | | | | $\Delta^D - 25$ |
| Difference $\Delta^D$ between the effect of the mixture and the difference $\Delta^D$ of the average effect of the individual active compounds | | | | $\Delta^D + 23$ |

Table 3d: Comparison of the effect of the mixture on all resistant and sensitive biotypes in PO application

| | Dose g of AS/ha | TTTTT resistant (n = 15) mean | TTTTT sensitive (n = 11) mean | Difference in sensitivities |
|---|---|---|---|---|
| (A) | 50 | 53 | 58 | $\Delta^D - 4$ |
| (B3) | 20 | 46 | 88 | $\Delta^D - 42$ |
| (A) + (B3) | 50 + 20 | 95 | 99 | $\Delta^D - 4$ |
| | | $E^c = 74$; $\Delta + 21$ | $E^c = 94$; $\Delta + 5$ | |
| Average difference $\Delta^D$ of the effect of the individual active compounds (Ø) | | | | $\Delta^D - 23$ |
| Difference $\Delta^D$ between the effect of the mixture and the difference $\Delta^D$ of the average effect of the individual active compounds | | | | $\Delta^D + 19$ |

Table 3e: Comparison of the effect of the mixture on all resistant and sensitive biotypes in PO application

| | Dose g of AS/ha | TTTTT resistant (n = 17) mean | TTTTT sensitive (n = 11) mean | Difference in sensitivities |
|---|---|---|---|---|
| (A) | 50 | 53 | 58 | $\Delta^D - 4$ |
| (B2) | 20 | 34 | 74 | $\Delta^D - 39$ |
| (A) + (B2) | 50 + 20 | 96 | 98 | $\Delta^D - 2$ |
| | | $E^c = 68$; $\Delta + 27$ | $E^c = 87$; $\Delta + 11$ | |
| Average difference $\Delta^D$ of the effect of the individual active compounds (Ø) | | | | $\Delta^D - 21$ |
| Difference $\Delta^D$ between the effect of the mixture and the difference $\Delta^D$ of the average effect of the individual active compounds | | | | $\Delta^D + 19$ |

Table 3f: Comparison of the effect of the mixture on all resistant and sensitive biotypes in PO application

| | Dose g of AS/ha | TTTTT resistant (n = 15) mean | TTTTT sensitive (n = 11) mean | Difference in sensitivities |
|---|---|---|---|---|
| (A) | 50 | 53 | 58 | $\Delta^D - 4$ |
| (B5) | 20 | 25 | 76 | $\Delta^D - 52$ |
| (A) + (B5) | 50 + 20 | 96 | 98 | $\Delta^D - 2$ |
| | | $E^c = 64$; $\Delta + 32$ | $E^c = 89$; $\Delta + 9$ | |
| Average difference $\Delta^D$ of the effect of the individual active compounds (Ø) | | | | $\Delta^D - 28$ |
| Difference $\Delta^D$ between the effect of the mixture and the difference $\Delta^D$ of the average effect of the individual active compounds | | | | $\Delta^D + 26$ |

$\Delta^D$ = TTTTT Ø resistant – TTTTT Ø sensitive

Table 4a: Comparison of the effect of the mixture on all resistant and sensitive biotypes in PE application

| | Dose g of AS/ha | TTTTT resistant (n = 16) mean | TTTTT sensitive (n = 11) mean | Difference in sensitivities |
|---|---|---|---|---|
| (A) | 12.5 | 52 | 68 | $\Delta^D - 16$ |
| (B) AE 1801486 | 20 | 33 | 76 | $\Delta^D - 43$ |

-continued

| | Dose g of AS/ha | TTTTT resistant (n = 16) mean | TTTTT sensitive (n = 11) mean | Difference in sensitivities |
|---|---|---|---|---|
| (A) + (B) | 12.5 + 20 | 95<br>$E^c = 65$;<br>$\Delta + 31$ | 98<br>$E^c = 89$; $\Delta + 9$ | $\Delta^D - 2$ |
| Average difference $\Delta^D$ of the effect of the individual active compounds (Ø) | | | | $\Delta^D - 29$ |
| Difference $\Delta^D$ between the effect of the mixture and the difference $\Delta^D$ of the average effect of the individual active compounds | | | | $\Delta^D + 27$ |

Table 4b: Comparison of the effect of the mixture on all resistant and sensitive biotypes in PE application

| | Dose g of AS/ha | TTTTT resistant (n = 16) mean | TTTTT sensitive (n = 11) mean | Difference in sensitivities |
|---|---|---|---|---|
| (A) | 12.5 | 52 | 68 | $\Delta^D - 16$ |
| (B4) | 20 | 29 | 82 | $\Delta^D - 53$ |
| (A) + (B4) | 12.5 + 20 | 92<br>$E^c = 64$;<br>$\Delta + 28$ | 98<br>$E^c = 93$; $\Delta + 5$ | $\Delta^D - 6$ |
| Average difference $\Delta^D$ of the effect of the individual active compounds (Ø) | | | | $\Delta^D - 34$ |
| Difference $\Delta^D$ between the effect of the mixture and the difference $\Delta^D$ of the average effect of the individual active compounds | | | | $\Delta^D + 28$ |

Table 4c: Comparison of the effect of the mixture on all resistant and sensitive biotypes in PE application

| | Dose g of AS/ha | TTTTT resistant (n = 16) mean | TTTTT sensitive (n = 11) mean | Difference in sensitivities |
|---|---|---|---|---|
| (A) | 12.5 | 52 | 68 | $\Delta^D - 16$ |
| (B1) | 20 | 32 | 75 | $\Delta^D - 43$ |
| (A) + (B1) | 12.5 + 20 | 92<br>$E^c = 64$;<br>$\Delta + 28$ | 99<br>$E^c = 91$; $\Delta + 7$ | $\Delta^D - 7$ |
| Average difference $\Delta^D$ of the effect of the individual active compounds (Ø) | | | | $\Delta^D - 29$ |
| Difference $\Delta^D$ between the effect of the mixture and the difference $\Delta^D$ of the average effect of the individual active compounds | | | | $\Delta^D + 22$ |

Table 4d: Comparison of the effect of the mixture on all resistant and sensitive biotypes in PE application

| | Dose g of AS/ha | TTTTT resistant (n = 16) mean | TTTTT sensitive (n = 11) mean | Difference in sensitivities |
|---|---|---|---|---|
| (A) | 12.5 | 52 | 68 | $\Delta^D - 16$ |
| (B3) | 20 | 24 | 75 | $\Delta^D - 51$ |
| (A) + (B3) | 12.5 + 20 | 86<br>$E^c = 60$;<br>$\Delta + 26$ | 95<br>$E^c = 90$; $\Delta + 4$ | $\Delta^D - 9$ |
| Average difference $\Delta^D$ of the effect of the individual active compounds (Ø) | | | | $\Delta^D - 34$ |
| Difference $\Delta^D$ between the effect of the mixture and the difference $\Delta^D$ of the average effect of the individual active compounds | | | | $\Delta^D + 25$ |

Table 4e: Comparison of the effect of the mixture on all resistant and sensitive biotypes in PE application

| | Dose g of AS/ha | TTTTT resistant (n = 16) mean | TTTTT sensitive (n = 11) mean | Difference in sensitivities |
|---|---|---|---|---|
| (A) | 12.5 | 52 | 68 | $\Delta^D - 16$ |
| (B2) | 20 | 22 | 73 | $\Delta^D - 50$ |
| (A) + (B2) | 12.5 + 20 | 85<br>$E^c = 60$;<br>$\Delta + 25$ | 89<br>$E^c = 89$; $\Delta \pm 0$ | $\Delta^D - 4$ |
| Average difference $\Delta^D$ of the effect of the individual active compounds (Ø) | | | | $\Delta^D - 33$ |
| Difference $\Delta^D$ between the effect of the mixture and the difference $\Delta^D$ of the average effect of the individual active compounds | | | | $\Delta^D + 29$ |

Table 4f: Comparison of the effect of the mixture on all resistant and sensitive biotypes in PE application

| | Dose g of AS/ha | TTTTT resistant (n = 16) mean | TTTTT sensitive (n = 11) mean | Difference in sensitivities |
|---|---|---|---|---|
| (A) | 12.5 | 52 | 68 | $\Delta^D - 16$ |
| (B5) | 20 | 22 | 73 | $\Delta^D - 47$ |
| (A) + (B5) | 12.5 + 20 | 85<br>$E^c = 62$;<br>$\Delta + 23$ | 94<br>$E^c = 90$; $\Delta + 4$ | $\Delta^D - 9$ |
| Average difference $\Delta^D$ of the effect of the individual active compounds (Ø) | | | | $\Delta^D - 31$ |
| Difference $\Delta^D$ between the effect of the mixture and the difference $\Delta^D$ of the average effect of the individual active compounds | | | | $\Delta^D + 22$ |

$\Delta^D$ = TTTTT Ø resistant − TTTTT Ø sensitive

CONCLUSION

For all resistant plant species examined, an additive or synergistic effect of the mixture was demonstrated both for PO and PE application (PO: $\Delta\pm 0-+60$; PE: $\Delta\pm 0-+100$). The level of assured efficacy against TSR- and NTR-resistant biotypes is markedly improved. Active compounds of HRAC groups B and L in the mixture are highly suitable for resistance management.

The mixture stabilizes the effect on sensitive and resistant plant species compared to the individual active compounds. Whereas the activity of the individual active compounds decreases by on average $\Delta^D-4\%$ to $-52\%$ (PO) or $\Delta^D-16\%$ to $-53\%$ (PE), the activity of the mixture decreases by only $\Delta^D-1$ to $-4\%$ (PO) or $\Delta^D-2$ to $-9\%$ (PE). The mixture has an advantage of Ø $\Delta^D+21\%$ (PO) and $\Delta^D+26\%$ (PE), respectively.

The invention claimed is:

1. The method for controlling harmful plants resistant to active compounds selected from the group consisting of the inhibitors of acetolactate synthase, acetyl coenzyme A carboxylase and 5-enolpyrovylshikimate-3-phosphate synthase, comprising applying to plants, plant parts, seeds, or an area under cultivation a herbicidal composition comprising
   A) indaziflam and
   B) chlorimuron-ethyl, wherein A and B applied together exhibits synergistic activity.

2. The method according to claim 1, wherein indaziflam is applied at an application rate of from 10 to 200 g/ha and chlorimuron-ethyl is applied at an application rate of from 2.5 to 100 g/ha.

3. The method according to claim 1, wherein indaziflam is applied at an application rate of from 10 to 150 g/ha and chlorimuron-ethyl is applied at an application rate of from 2.5 to 75 g/ha.

4. The method according to claim 1, wherein indaziflam is applied at an application rate of from 10 to 100 g/ha and chlorimuron-ethyl is applied at an application rate of from 2.5 to 40 g/ha.

5. The method according to claim 1, wherein the herbicidal composition further comprises one or more further active crop protection compounds.

6. The method according to any of claim 1, wherein the herbicidal composition further comprises one or more auxiliaries and/or formulation aids customary in crop protection.

7. A herbicidal composition comprising
A) indaziflam and
B) chlorimuron-ethyl effective in controlling harmful plants resistant to active compounds selected from the group consisting of the inhibitors of acetolactate synthase, acetyl coenzyme A carboxylase, photosynthesis at photosystem II, microtubuli arrangement, cell division or 5-enolpyrovylshikimate-3-phosphate synthase, wherein A and B together exhibits synergistic activity.

8. The composition according to claim 7, wherein indaziflam is applied at an application rate of from 10 to 200 g/ha and chlorimuron-ethyl is applied at an application rate of from 2.5 to 100 g/ha.

9. The composition according to claim 7, wherein indaziflam is applied at an application rate of from 10 to 150 g/ha and chlorimuron-ethyl is applied at an application rate of from 2.5 to 75 g/ha.

10. The composition according to claim 7, wherein indaziflam is applied at an application rate of from 10 to 100 g/ha and chlorimuron-ethyl is applied at an application rate of from 2.5 to 40 g/ha.

11. The composition according to claim 7, wherein the herbicidal composition further comprises one or more further active crop protection compounds.

12. The composition according to claim 7, wherein the herbicidal composition further comprises one or more auxiliaries and/or formulation aids customary in crop protection.

13. A herbicidal composition comprising
A) indaziflam and
B) chlorimuron-ethyl, wherein A and B together exhibits synergistic activity.

14. The herbicidal composition according to claim 13, further comprising one or more further active crop protection compounds.

15. The herbicidal composition according to claim 13, further comprising one or more auxiliaries and/or formulation aids.

* * * * *